United States Patent [19]

Muetterties et al.

[11] 4,296,949
[45] Oct. 27, 1981

[54] ROTATABLE CONNECTING DEVICE FOR I.V. ADMINISTRATION SET

[75] Inventors: Andrew J. Muetterties, Gages Lake; John L. Vcelka, Zion; Wayne R. Kelsey, Des Plaines, all of Ill.

[73] Assignee: Abbott Laboratories, North Chicago, Ill.

[21] Appl. No.: 64,141

[22] Filed: Aug. 6, 1979

[51] Int. Cl.³ .............................................. F16L 19/02
[52] U.S. Cl. ........................................ 285/18; 285/93; 285/332; 285/386; 128/214 R
[58] Field of Search .............. 285/332, 386, 387, 388, 285/18, 93; 128/214 R

[56] References Cited

U.S. PATENT DOCUMENTS

| | | | |
|---|---|---|---|
| Re. 29,376 | 8/1977 | Hiszpanski | 285/332 X |
| 645,692 | 3/1900 | Richardson | 285/332 X |
| 1,742,497 | 1/1930 | Dickinson | 285/332 X |
| 2,229,669 | 1/1941 | Oremus | 285/386 X |
| 2,374,348 | 4/1945 | Harding | 285/332 X |
| 2,511,396 | 6/1950 | Brekke | 285/332 |
| 3,201,148 | 8/1965 | Shurtleff | 285/3 |
| 3,514,131 | 5/1970 | McKinney | 285/332 |
| 3,616,866 | 11/1971 | Verheul | 285/332 X |
| 3,640,551 | 2/1972 | Shakesby | 285/39 |
| 3,977,708 | 8/1976 | Jopp | 285/342 |
| 4,014,568 | 3/1977 | Carter et al. | 285/39 |
| 4,133,312 | 1/1979 | Burd | 285/332 X |

Primary Examiner—Thomas F. Callaghan
Attorney, Agent, or Firm—Robert L. Niblack; Neil E. Hamilton

[57] ABSTRACT

A rotatable connecting device which provides for quick and positive interfitment between a venipuncture unit and an intravenous administration set without rotation or twisting of the venipuncture unit or intravenous tubing. A rotatable collar is provided on one of the members constituting the connecting device and is captively held thereon while permitting longitudinal movement. Frictional engaging means are disposed on the body member retaining the collar as well as the collar to provide an interference fitment. Internal threads are defined in the rotatable collar for engagement with a flange member disposed on the catheter hub. A luer lock fitment is afforded between the catheter member and the member carrying the rotatable collar.

20 Claims, 12 Drawing Figures

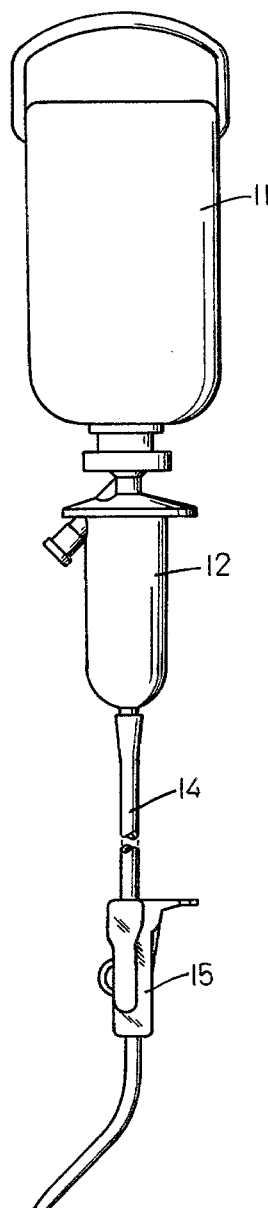
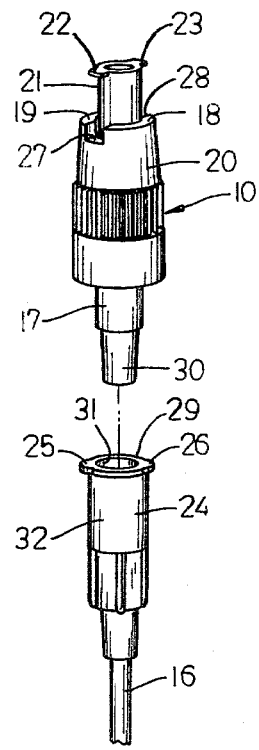
FIG. 1
FIG. 2

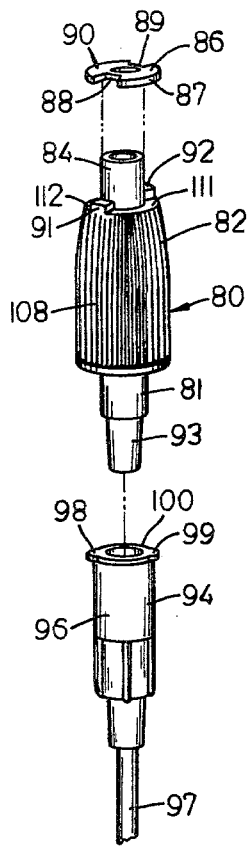
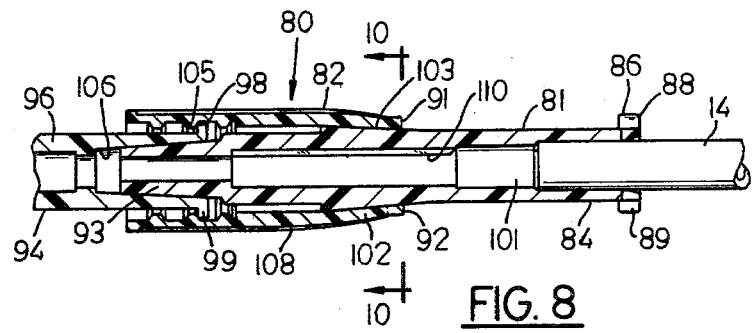
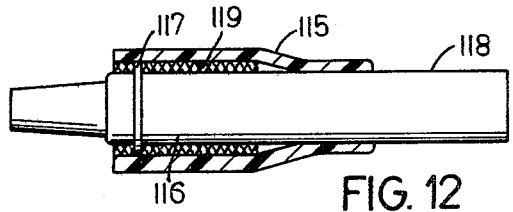
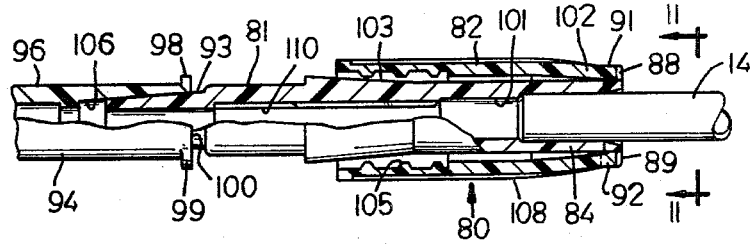
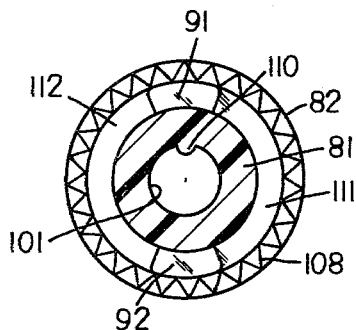
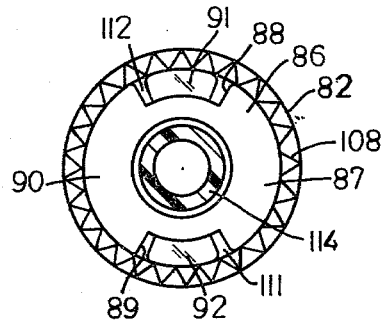

ROTATABLE CONNECTING DEVICE FOR I.V. ADMINISTRATION SET

BACKGROUND OF THE INVENTION

This invention relates to a connecting device which can quickly and effectively interconnect an I.V. administration set with a venipuncture unit. More particularly, this invention relates to a rotatable connector device for I.V. tubing which will permit a quick connection between an I.V. administration set and a catheter without twisting the catheter tubing or the I.V. tubing and at the same time afford a fluid-tight connection.

A connection between an I.V. set and a venipuncture device such as a catheter is usually accomplished by the frictional engagement of a male fitment on the administration set and the female fitment on the venipuncture device. While a reasonably secure and leakfree interfitment is accomplished, this type of connection is susceptible to disconnection from manipulation or internal pressure. Rotatable connecting collar members of the slidable and nonslidable type are known for use in interconnecting components in I.V. administration sets. A slidable device is currently being marketed by a company known as Vygon, which is located in France. A nonslidable unit of this type used in conjunction with a stopcock is available from the Pharmaseal Company in Glendale, Calif. Rotatable interconnecting devices for tubular members are also described in U.S. Pat. Nos. 3,201,148; 3,616,866; 3,640,551; 3,977,708 and 4,014,568. While these patents describe various types of tubular interconnecting members, problems arise if the rotatable collar is not freely manipulative in that the luer fitment does not lock and the collar can become cross-threaded with the catheter. None of the prior devices offers a connecting unit specifically designed for use in conjunction with I.V. tubing and a venipuncture device which is simplified in its construction and will permit the fast and fluid-tight connection between the two units and without rotation of the units or connected tubing. Neither does the prior art afford a connection between an I.V. set and a catheter wherein alignment prior to interconnection is easily and quickly facilitated.

It is an advantage of the present invention to provide a novel connecting device for interconnecting an I.V. set with a venipuncture unit wherein the interconnection can be made with a minimum amount of manipulation. Other advantages are an interconnecting device for I.V. tubing and a catheter unit which obviates a twisting of the catheter tubing or the I.V. tubing during interconnection; a fluid-tight connection between the venipuncture device and the I.V. tubing which offers the operator the option of use as a secondary security system so that the fitment will not become disconnected during normal usage; a connecting device which is easily fabricated with a minimum number of parts and readily placed on an I.V. administration set; a connecting unit which can be fabricated from resinous plastic materials so as to be disposable and not appreciably add to the cost of an I.V. set.

SUMMARY OF THE INVENTION

The foregoing advantages are accomplished and the shortcomings of the prior art are overcome by the connecting device of this invention which comprises two members each having a fluid passage therethrough. A tapering interfitment means such as male and female luer fitments are provided for fluid-tight engagement. A length of tubing is secured to at least one member opposite the interfitment means. A flange extends from one of the members and preferably that having catheter tubing. A collar member is rotatably mounted on the other member and has internal threads for engagement with the flange. The rotatable member is captively held on one of the members in such a manner as to permit free movement along the longitudinal axis thereof while retaining the collar thereon. The captive means includes frictional engagement means defined by the member mounting the collar and the collar for interference fitment. When the luer lock portions are interengaged, the collar member will engage the flange and upon rotation of the collar the luer lock portions will be forced into fluid-tight engagement and the frictional engaging means of the mounting and collar members will engage without rotation of the catheter hub or the body member connected to the I.V. tubing. In a preferred embodiment, the rotatable collar is fixed to the body portion of the connecting device attached to the I.V. tubing and a flange or flanges extend from the hub of the catheter. In another embodiment, a portion of the captive means for the rotatable collar is formed as a frangible portion on the collar member.

BRIEF DESCRIPTION OF THE DRAWINGS

A better understanding of the connecting device of this invention will be accomplished by reference to the drawings wherein:

FIG. 1 is a perspective view of a parenteral solution administration device showing the connecting device of this invention operatively connecting the administration device with a catheter.

FIG. 2 is an enlarged perspective view of the connecting device shown in FIG. 1.

FIG. 7 is a view similar to FIG. 2 except showing still another embodiment.

FIG. 8 is a view similar to FIG. 6 except of the connecting device shown in FIG. 7.

FIG. 9 is a view in partial vertical section of the connecting device shown in FIG. 8 but with the collar member retracted and engaging the flanges of the collar retainer.

FIG. 10 is an enlarged view in vertical section taken along line 10—10 of FIG. 8.

FIG. 11 is an enlarged view in vertical section taken along line 11—11 of FIG. 9.

FIG. 12 is an enlarged detailed view of a further embodiment of a rotatable collar and catheter hub for use in the connecting device of this invention.

DESCRIPTION OF ONE EMBODIMENT

Figure 3:
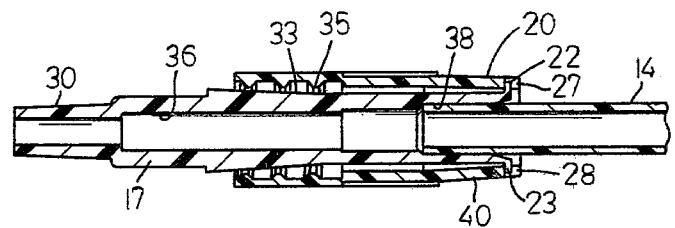
FIG. 3 is a view in vertical section illustrating the member of the connecting device having the rotatable collar member.

Proceeding to a detailed description of one of the embodiments of the present invention, the connecting device 10 is shown in FIG. 1 in connection with a parenteral solution container 11 having connected thereto a combined piercing pin and drip chamber 12. A length of tubing 14 extends from drip chamber 12 to which is attached a flow control clamp 15. Tubing 14 is secured to the connecting device 10 to which is interconnected catheter 24 having catheter tubing 16.

Figure 4:
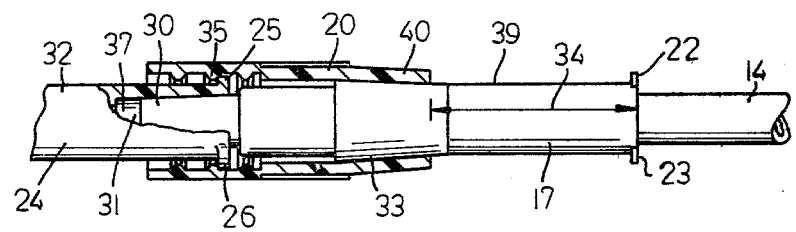
FIG. 4 is a view in partial vertical section showing the member with the rotatable collar engaging the hub of a catheter device.

Referring specifically to FIG. 2, it will be noted that connecting device 10 includes a rotatable collar 20 extending over a body member 17 of a catheter adapter. Shoulder members in the form of flanges 22 and 23 project outwardly from one end of body member 17 and an external luer fitment 30 from the other end. Rotatable collar 20 includes two slots 27 and 28 surrounded by arcuate walls 18 and 19, for accommodating flanges 22 and 23 in a captive manner. External luer fitment 30 is constructed to fit into catheter hub 32 which has an internal luer fitment 31 (See FIG. 4). Catheter hub 32 has two extending flanges 25 and 26 interconnected by an annular portion 29. Referring specifically to FIGS. 3 and 4, it will be noted that body member 17 has a tapering wall 33 for interference fitment with inwardly tapering wall portion 40 of rotatable member 20. Also, rotatable member 20 has internal threads 35 for threaded engagement with flanges 25 and 26 when the external luer fitment 30 of body member 17 is seated in internal luer fitment 31 of catheter hub 32. A fluid passage 36 extends through body member 17 and communicates with tubing 14 seated in chamber 38. A fluid passage 37 also is provided throughout catheter 24.

Figure 5:
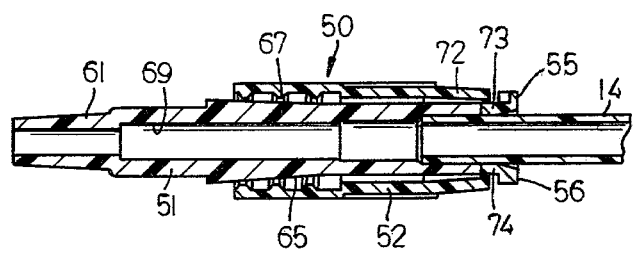
FIG. 5 is a view similar to FIG. 3 except showing another embodiment.
Figure 6:
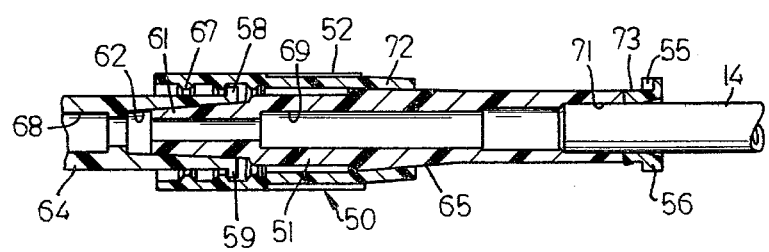
FIG. 6 is a view of one portion of the connecting device with the rotatable collar illustrated in FIG. 5 and engaging the catheter unit such as described in FIG. 4.

Connecting device 50 shown in FIGS. 5 and 6 is similar to that of device 10 in that it has a rotatable collar 52 positioned over body member 51. A tapering wall 65 is provided on body member 51 for an interference fitment with inwardly tapering portion 72 of rotatable member or collar 52. Flanges 55 and 56 extend from retaining member 74 which is originally interconnected to rotatable collar 52 by means of frangible portion 73. Internal threads 67 are disposed in rotatable collar 52 and an external luer fitment 61 extends from body member 51 with a fluid passage 69 interconnecting tubing 14. A catheter hub 64 is engaged by rotatable collar 52 when the internal threads 67 engage flanges 58 and 59. The external luer fitment 61 of body 51 will seat in internal luer fitment 62 of catheter hub 64 which has a fluid passage 68 in communication with catheter tubing 16.

FIGS. 7–11 illustrate another embodiment of the invention wherein connecting device 80, as is true of devices 10 and 50, includes a body member 81 with rotatable collar 82 positioned thereon having knurling 108. Body member 81 has an end portion 84 to which is affixed, such as by ultrasonic sealing, a retaining collar 86 after rotatable collar 82 is placed thereon. Slots 88 and 89 are provided in collar 86 separated by shoulder or flange portions 87 and 90 which will receive flanges 91 and 92, of rotatable collar 82, and rotatable collar 82 will be captively held on body member 81 by contact of arcuate walls such as 111 and 112 disposed between flanges 91 and 92 contacting shoulder portions 90 and 87 of retainer 86. An external luer fitment 93 extends from body member 81 for sealing engagement with catheter 94 and the internal luer fitment 106 of catheter hub 96. Flanges 98 and 99 interconnected by annulus 100 extend from catheter hub 96 at one end and catheter tubing 97 from the opposing end. As best seen in FIG. 8, a fluid passage 101 extends through body member 81 and is in fluid communication with I.V. tubing 14. Collar 82 has an inwardly tapering portion 102 for frictional engagement with tapering wall 103 of body member 81. Internal threads 105 are disposed in collar 82 for engagement with flanges 98 and 99 of catheter 94.

Referring to FIG. 10, it will be noted that body member 81 has a bevel indicator 110 in the form of a projection extending into fluid passage 101. The purpose of the bevel indicator 110 is to indicate the position or bevel of a needle or stylet as it is placed in the vein during venipuncture. So that the bevel indicator is visible, body member 81 will be composed of a transparent material.

FIG. 12 illustrates another manner for assuring that the rotatable collar such as 115 will remain in contact with wall 116 of male catheter adapter 118. For this purpose frictional engaging means in the form of a ridge 117 is disposed on wall 116 of catheter adapter 118 and internal knurlings 119 are provided in collar 115 for interengagement. Ridge 117 and knurlings 119 can be utilized in place of tapering walls 33, 65 and inwardly tapering portions 40, 72.

OPERATION

A better understanding of the advantages of the connecting device of this invention will be had by a description of its operation. Connecting device 10 will operate in substantially the same manner as connecting devices 50 and 80. It will be appreciated that in most instances body portion 17 and rotatable collar 20 will be interconnected to tubing 14 and supplied independently of catheter 16 and hub 32. At the time of use, catheter tubing 16 will have already been inserted into an appropriate vein by the usual methods. When it is desired to administer the contents of solution container 11, all that is required is to orientate external luer fitment 30 with catheter hub 32 as indicated in FIG. 2. Collar 20 will be in a position as indicated in FIG. 2 to expose a surface area such as 21 to be gripped by the fingers of one hand while the remaining fingers will grip rotatable member 20. Catheter hub 32 will be gripped with the other hand. After the appropriate interconnection between external luer fitment 30 and internal luer fitment 31 of hub 32, rotatable member 20 will be rotated whereby internal threads 35 will engage flanges 25 and 26. Rotation will be continued until inwardly tapering wall 40 of rotatable member 20 engages tapering wall 33 of body member 17 to thereby firmly retain the external and internal luer fitments 30 and 31 respectively, in a fluid-tight engagement such that they will not become disengaged without a turning of the collar 20. Through the frictional engagement of inwardly tapering portion 40 and tapering wall 33 only intentional rotation of the rotatable member will cause disengagement of the rotatable member 20 and additional force would be required to dislodge the previously described luer fitment. It will be appreciated that collar 20 is captively held on body member 17 by means of flanges 22 and 23 at one end engaging the ends of slots 27 and 28 and the engagement at the opposing end of inwardly tapering portion 40 and tapering wall 33.

An important feature of this invention is in permitting the longitudinal movement of the collar over a substantial portion of body member 17 such as designated by double headed arrow 34 to thereby allow alignment of external luer fitment 30 with internal luer fitment 31 prior to engagement of internal threads 35. This is partially provided by straight walled body section 39. With the proper interfitment, the collar is then brought forward so that the threads 35 will engage flanges 25 and 26 and rotation continued until the contact of inwardly tapering portion 40 and tapering wall 33. All of the foregoing, it will be noted, will be effected without the undesired rotation of either catheter hub 32 and its associated tubing 16 or any rotation of I.V. tubing 14.

The operation of connecting unit 50 is substantially the same as that previously described for unit 10 except that in its original fabrication, the inwardly tapering portion 72 of rotatable collar 52 will be interconnected to retaining member 74 by means of a frangible portion 73. During fabrication, collar 52 will be fractured from retaining member 74 and will break away from member 74 to become freely movable therefrom with the retaining member 74 remaining and ultrasonically attached to body member 51. In all other respects, the interengagement of internal threads 67 with flanges 58 and 59 of catheter hub 64 will be the same as described for connecting device 10 as well as the travel of collar 52 over body 51 and the frictional engagement of inwardly tapering portion 72 and tapering wall 65.

Unit 80 will operate in basically the same manner as previously described for unit 10 in the engagement between body member 81 and catheter 94. One major difference between unit 80 and units 10 and 50 is in the initial fabrication. In unit 80, collar 82 will first be placed over body member 81 and, as indicated in FIG. 7, collar retainer 86 will be ultrasonically sealed to end portion 84 of body member 81. It will be further observed that the placement of flanges 91 and 92 on collar 82 as well as slots 88 and 89 on retainer 86 are the opposite of the corresponding members in unit 10. In any event, they serve the same purpose of providing a wrench effect to free the frictional engagement between the external and internal luer fitments such as 93 and 106, respectively, when the flanges 91 and 92 are positioned to engage the slots 88 and 89 of retainer 86 and a rotation imparted to collar 82 while catheter 94 is held stationary. The same torque effect is accomplished in unit 50 between flanges 55 and 56 and collar 52 except in this instance the flanges extend parallel with the longitudinal axis of body member 51 and will be accommodated by apertures (not shown) at the end of inwardly tapering portion 72 of collar 52.

The preferred materials for composing body members 17, 51 and 81 as well as their associated collars 20, 52, and 82 are rigid polyvinyl chloride. However, other plastic materials such as polycarbonate, ABS or styrene could be utilized. In the instance of connecting device 50, it will be appreciated that frangible portion 73 will be initially ultrasonically sealed to body member 51 with weakened portions provided so as to afford a breaking away of collar 52 from frangible portion 73.

The connecting device of this invention has been described for use with a catheter adapter. It will be appreciated that the same advantage can be obtained when it is employed in conjunction with a stopcock unit to be used with an I.V. administration set. Further, the connecting device has application with a wide variety of administration devices such as arterial infusion lines, central vein lines, pressure infusion applications, pediatric administration sets as well as special sets where the patient is ambulatory.

It will thus be seen that through the present invention there is now provided a connecting device for an I.V. administration set and catheter tubing wherein a connection as well as disconnection can be made in a fast and efficient manner and without rotation of the catheter or the I.V. tubing. The connecting device of this invention can be readily molded and fabricated at little cost so as to not appreciably add to the cost of the I.V. administration set yet will be disposable. Interfitment of the interconnecting device is facilitated by affording longitudinal movement of the collar over the connecting device body member so as to afford proper alignment with the flanges on the catheter hub prior to engagement of the internal screw threads in the collar member.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A connecting device for an intravenous administration set comprising:
   a first member defining a fluid passage means and having a longitudinal axis;
   a second member defining a fluid passage means and having a longitudinal axis;
   tapering interfitment means constructed and arranged with respect to each said member for fluid-tight engagement;
   a length of tubing secured to at least one member opposite said tapering interfitment means;
   a flange extending from one of said first or second members adjacent said tapering interfitment means;
   a collar member alternately and rotatably mounted on one of said first or second members opposite said flange, said collar member having internal threads for engagement with said flange; and
   captive means operatively associated with one of said members and said collar member to permit free movement along the longitudinal axis of said member while retaining said collar on said member yet permitting rotatable engagement with said flange, said captive means including a tapering surface defined by said member mounting said collar for interference therewith, said captive means constructed and arranged to permit said collar member to be positioned a substantial distance away from said tapering interfitment means carried by said member mounting said collar member for complete exposure for sterilization purposes, said captive means further including cooperating means defined by said member mounting said collar member and said collar member to provide an interlocking mechanism, said cooperating means positioned on said collar member opposite said internal threads and on said mounting member opposite said tapering surface;
   so that when said tapering interfitment means is interengaged, said collar member will engage said flange and upon rotation of said collar the interfitment means will be forced into fluid-tight engagement and said collar member will engage said tapering surface without rotation of said first or second members, and upon a reverse rotation of said collar member and movement of said collar member away from said flange, said interlocking mechanism will interengage whereby rotation of said collar will cause rotation of said member mounting said collar without rotation of said member with said flange.

2. The connecting device as defined in claim 1 wherein said tapering interfitment means is defined by an internal and external luer fitment with said internal luer fitment and said flange is positioned on said first member and said collar and said external luer fitment positioned on said second member.

3. The connecting device as defined in claim 2 wherein said interlocking mechanism includes shoulder members carried by said second member and spaced from said tapering surface of said mounting member.

4. The connecting device as defined in claim 2 wherein said flange is defined by two flanges and extends from said first member positioned immediately adjacent an entrance to said internal luer fitment and interconnected by an annular portion.

5. The connecting device as defined in claim 3 wherein said second member includes an internal chamber for seating engagement with said tubing.

6. The connecting device as defined in claim 3 wherein said shoulder members are defined by two oppositely positioned and extending flange members and said collar is defined by two opposing slots constructed and arranged to receive said flange members.

7. The connecting device as defined in claim 6 wherein said flange members extend outwardly from said second member.

8. The connecting device as defined in claim 6 wherein said opposing slots extend parallel with the longitudinal axis of said second member and said flange members are connected to said second member by a frangible section.

9. The connecting device as defined in claim 3 wherein said shoulder members are defined by two oppositely positioned and extending flange members separated by two opposing slots and said collar is defined by two extending flanges constructed and arranged to be received in said slots.

10. The connecting device as defined in claim 3 wherein said collar includes an inwardly tapering portion for contact with said tapering surface defined by said mounting member.

11. The connecting device as defined in claim 1 wherein said internal threads of said collar member are continuous.

12. The connecting device as defined in claim 10 wherein said member mounting said collar includes a straight walled body section continuous with said tapering surface.

13. The connecting device as defined in claim 1 wherein said length of tubing is connected to said first member and defines a catheter tubing and said length of tubing is connected to said second member and is intravenous plastic tubing.

14. A connecting device for an intravenous administration set adapted to interconnect with a projecting flange of a catheter unit having an internal luer tapering chamber comprising:
a mounting member defining a fluid passage means and a longitudinal axis;
a length of tubing secured to said member;
a collar member rotatably on said member, said collar member having internal threads for engagement with said flange of said catheter unit;
captive means operatively associated with said member to permit free movement along the longitudinal axis thereof while retaining said collar on said member yet permitting rotatable engagement with said flange;
a luer tapering extending member for fluid-tight fitment into said internal luer tapering chamber of said catheter unit; and
said captive means including a tapering surface defined by said member for interference with said collar member, said captive means constructed and arranged to permit said collar member to be positioned a substantial distance away from said luer tapering extending member for complete exposure for sterilization purposes, said captive means further including cooperating means defined by said mounting member and said collar member to provide an interlocking mechanism, said cooperating means positioned on said collar member opposite said internal threads and on said mounting member opposite said tapering surface;
so that when said luer tapering extending member is placed in said luer tapering chamber, said collar member will engage said flange and upon rotation of said collar said luer tapering extending member will be forced into fluid-tight engagement and said collar member will contact said tapering surface, and upon a reverse rotation of said collar member and movement of said collar member away from said flange, said interlocking mechanism will interengage whereby rotation of said collar will cause rotation of said mounting member without rotation of said catheter unit.

15. The connecting device as defined in claim 14 wherein said interlocking mechanism includes a shoulder member carried by said mounting member.

16. The connecting device as defined in claim 15 wherein said shoulder member is defined by two opposing flanges and said collar member includes two slot portions constructed and arranged to receive said flanges.

17. The connecting device as defined in claim 16 wherein said flanges are formed as a frangible portion of said mounting member.

18. The connecting device as defined in claim 14 wherein said interlocking mechanism provides a wrench effect between said captive means and said collar member.

19. The connecting device as defined in claim 14 wherein said mounting member further includes a bevel indicator means.

20. The connecting device as defined in claim 14 wherein said frictional engaging means is defined by knurlings and a ridge operatively associated with said collar and mounting members.

* * * * *

Notice of Adverse Decision in Interference

In Interference No. 101,097, involving Patent No. 4,296,949, A. J. Muetterties, J. L. Vcelka and W. R. Kelsey, ROTATABLE CONNECTING DEVICE FOR I.V. ADMINISTRATION SET, final judgment adverse to the patentees was rendered Apr. 28, 1986, as to claims 1-4, 6, 7, 10, 11, 13-16 & 18.
*[Official Gazette July 15, 1986.]*